United States Patent

Tanaka et al.

[11] Patent Number: 5,571,967
[45] Date of Patent: Nov. 5, 1996

[54] TERMITE DETECTING DEVICE AND A METHOD OF DETECTING TERMITES

[75] Inventors: Kunio Tanaka, Ikeda; Yuji Dohi, Nara; Akira Okamoto, Kitakatsuragi-gun; Katsushi Morimoto, Nara; Gouichi Kagiyama, Izumi, all of Japan

[73] Assignee: Sharp Kabushiki Kaisha, Osaka, Japan

[21] Appl. No.: 267,940

[22] Filed: Jul. 6, 1994

[30]  Foreign Application Priority Data

| Jul. 7, 1993 | [JP] | Japan | 5-167568 |
| Oct. 27, 1993 | [JP] | Japan | 5-268609 |
| Mar. 24, 1994 | [JP] | Japan | 6-053551 |
| Apr. 15, 1994 | [JP] | Japan | 6-077531 |

[51] Int. Cl.$^6$ .......................... G01N 3/40; G01N 29/00
[52] U.S. Cl. ................ 73/587; 73/81; 73/865.8; 340/573
[58] Field of Search ............ 73/587, 661, 659, 73/78, 81, 865.8, 866; 200/61.42; 340/573, 686

[56]  References Cited

U.S. PATENT DOCUMENTS

| 4,111,039 | 9/1978 | Yamawaki et al. | 73/81 |
| 4,159,640 | 7/1979 | Levegue et al. | 73/81 |
| 4,991,439 | 2/1991 | Betts | 73/587 |
| 5,024,832 | 6/1991 | Omata et al. | 424/84 |
| 5,263,220 | 11/1993 | Campbell | 73/865.8 |
| 5,285,688 | 2/1994 | Robbins et al. | 73/587 |
| 5,329,726 | 7/1994 | Thorne et al. | 43/124 |

FOREIGN PATENT DOCUMENTS 59-3353  1/1984  Japan .................... 73/865.8

OTHER PUBLICATIONS

R. L. Ethington, "Is Wood Hardness Affected by Preservative Treatment?" *Forest Products Journal*, vol. 22, No. 5, May 1972, pp. 60–61. Copy in 73/81.

*Primary Examiner*—John E. Chapman

[57]  ABSTRACT

The termite detecting device is placed in an expected invading passage for detecting damage or destruction caused by termites. One configuration of the device includes: a detecting wood sample for attracting termites; a detecting terminal being pressed against the detecting wood sample while the detecting wood sample is supplied with water as required; and a magnetic circuit capable of being opened and closed by the movement of the detecting terminal. When the detecting wood sample is eaten and damaged by termites and becomes fragile, the detecting terminal sinks into the detecting wood sample by virtue of a pressing force and the magnetic circuit is made open. As a result, the device detects the existence of termites. Alternatively, another configuration of the termite detecting device detects vibrations caused by termites so as to detect the invasion of termites. In either device, when a valid signal from a magnetic sensor or a vibration sensor is issued, an indicator disposed in a house is activated to warn in response to the sensor signal. Alternatively the valid signal is transmitted by way of telephone line, etc., to a control center. Thus, the device warns the user of the invasion by termites in an early stage so that the user may take a quick action.

34 Claims, 9 Drawing Sheets

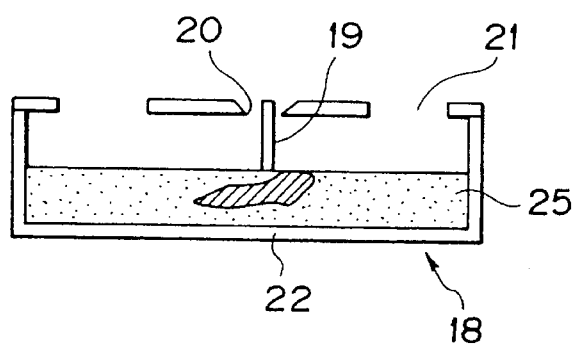
FIG. 1A
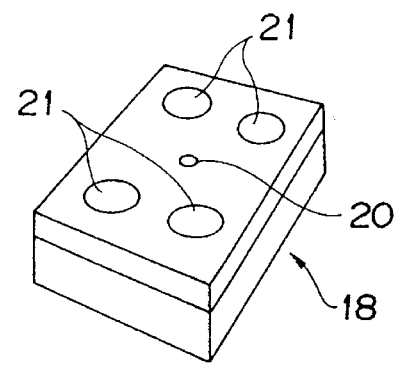
FIG. 1B
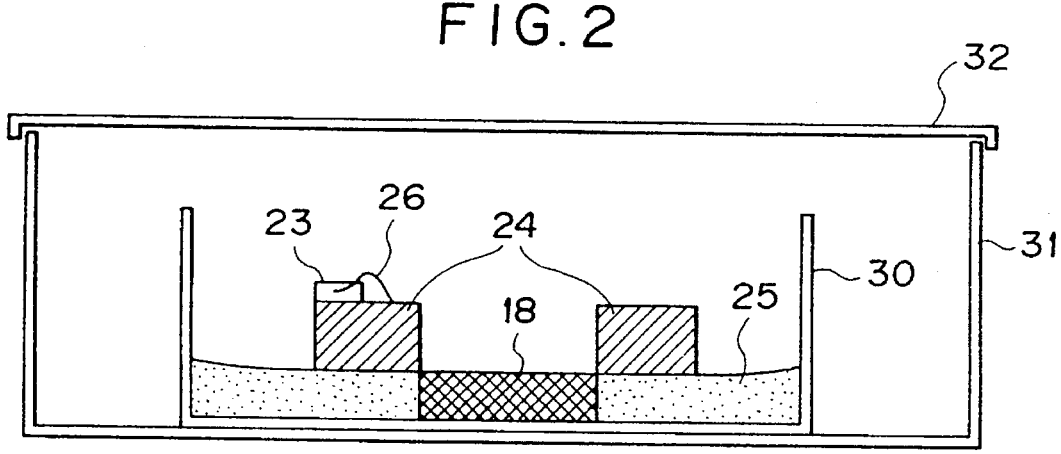
FIG. 2
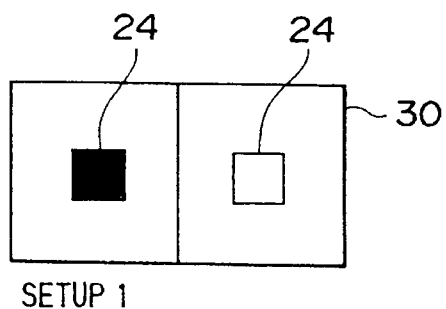
SETUP 1
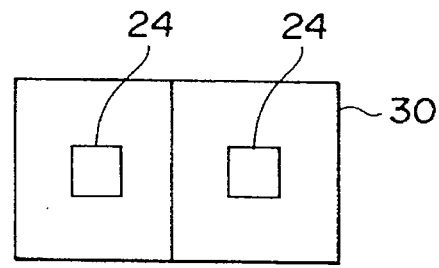
SETUP 2
■ ---- WATER-SUPPLIED SECTION
□ ---- SECTION WITHOUT WATER
FIG. 3

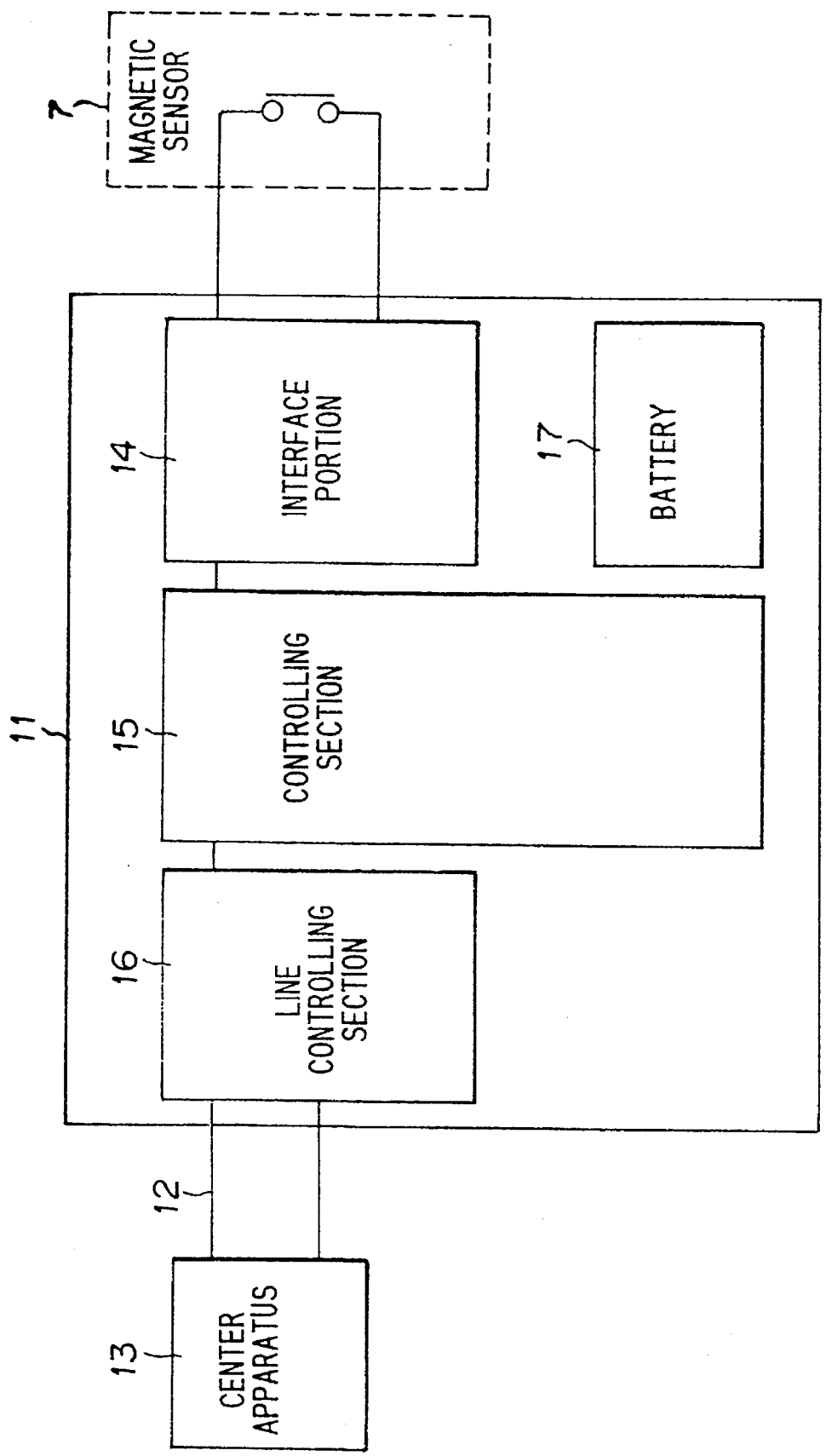

TERMITE DETECTING DEVICE AND A METHOD OF DETECTING TERMITES

BACKGROUND OF THE INVENTION (1) Field of the Invention

The present invention relates to a termite detecting device and a method of detecting termites whereby damage caused by termites entering houses is located and identified.

(2) Description of the Prior Art

Termites exhibit negative phototaxis (or move away from light) so that they nest in unobservable, dark places to lead their lives. Therefore, it is very hard to detect invasions of termites into houses.

Termites are insects that belong to a family of Isoptera. As there are reportedly about 2050 species of termites scattered all over the world, they are known as a common harmful organism which damages buildings in both Occidental and Oriental countries.

For instance, mainly, two species of termites inhabit Japan, namely, 'Yamato-Shiroari termites' and 'Ie-Shiroari termites'. These are called underground termites, which nest under the ground to eat away wood of houses in dark places to hollow out the inside of wood.

As termites have swarming behavior, a large number of the Yamato-Shiroari termites, for example, forming huge aggregation, happen to swarm from their nest after the emergence in April and May. In most cases, this would be the first notice or finding of the invasion of the termites.

That is, in practice, it is not until a large number of termites in the winged form (winged ants) swarm away in spring from their nest that the habitant notices the existence. Therefore, at the time, damage to the house would be in the advanced stage and it would, in most cases, be too late to deal with the damage.

In order to deal with this, for detecting invasions of termites in the early stage, possible structures to be damaged have been subjected to 'cavity sound test', 'detecting test of termites on eating or destructive action sounds', 'visual observation under floors', or 'periodical visual observations of testing wood set in expected invading passages of termites to a building under test'.

Nevertheless, of all the aforementioned early-stage detecting means of termites, 'cavity sound test' and 'detecting test of termites on eating or destructive action sounds' require skillful staffs to go to the place to be tested so as to examine all the possible parts of the structure of the building. Accordingly, these methods take a great deal of payment and labors. Particularly, in the case of 'detecting test of termites on eating or destructive action sounds', it would be difficult to surely detect the existence of termites when the detection was performed in an inactive period (especially in winter) of the termites or at an inactive time of them.

As depending upon the locations, the most active period and time of termites is typically considered to be from April to October during the time from nightfall to midnight. Other than that period and that time, termites are hard to detect.

In addition, most of the houses based upon the recent architectural techniques have minimal underfloor spaces, so that the underfloor space is hard for an inspector to enter, thus making it extremely difficult to execute 'visual check'. Besides, as to bathrooms where termites are most likely to invade for feeding, it is impossible to enter the underfloor space thereof, therefore, the visual check of the bathroom is actually unfeasible.

With respect to the method by 'periodical visual observations of testing wood set in expected invading passages of termites to a building under test', since a professional staff must periodically carry out visual inspections of a considerable number of the testing wood for each house by pulling them out from the earth, this work requires a rather high cost and much labor.

In order to solve the problems stated above, various kinds of proposals have been made other than the aforementioned method disclosed in Japanese Patent Application Laid-Open Sho 63 No. 56240 in which, as stated above, whether or not termites exist in the wood placed in the intruding paths is observed. Another method, as disclosed in Japanese Utility Model Application Laid-Open Hei 1 No. 118677 and Japanese Patent Publication Hei 4 No. 21449, is that, termite-detectors formed of a wooden container with a termite-detecting sample inserted into a hollowed inside thereof are buried in the earth in such positions as to be expected to be invading passages of termites, and the thus accommodated, detecting samples are periodically or irregularly drawn out so as to be visually observed for checking the existence of termites. This method is to take advantage of the taxis for channel of termites which causes termites to be attracted to a clearance formed between the wooden container and the inserted detecting sample.

Another alternative method is disclosed in Japanese Utility Model Laid-Open Sho 61 No. 142586. According to the disclosure, two or more than two termites' favorite wooden pieces are jointed together by a jointing means in a detachable manner so as to form one or more joint portions. The thus formed joint portions are checked on termite-eaten damage, periodically, in order to monitor the activity situation of termites.

A method of inspecting damages by general wood-destroying insects, as is disclosed in Japanese Patent Application Laid-Open Hei 2 No. 251750, is that the inside of a wood under test is inspected from the outside using a supersonic non-destructive tester, etc., to examine whether or not there is any cavity or hollow inside the wood. An alternative method, as is disclosed in Japanese Patent Application Laid-Open Hei 3 No. 102257, is that the sound from the inside of a wood being damaged is observed with an acoustic emission sensor (which will hereinafter be abbreviated as A.E. sensor) being attached to the wood.

On the other hand, U.S. Pat. No. 4,895,025 discloses a method in which vibrations induced by wood article destroying insects during their feeding are amplified to an audible level and the thus obtained vibratory sounds are analyzed and compared with other records of known destructive insects on the basis of the fact that vibratory sounds generated during feeding are different depending upon the species of insects, to thereby determine the probable species of insect and its location. This disclosure exemplified a comparison of vibratory behavior by termites to that caused by carpenter ants.

By the way, if no termite detector of the above proposed kinds is set from the beginning, there is no other way for a habitant to know the existence of termites than witnessing a swarm of termites after the destruction has reached an advanced level. And if he or she found them, a lot of swarmings of termites are found in various places in April and May because swarming action of termites occurs all at once in this period. Therefore, the traders of removing termites would have a rush of claims and questions as well as requests for spraying insecticides in this limited period so that it was very difficult for the traders to quickly deal with all such requests.

The above described various termite-detectors have been proposed to deal with the problem just mentioned above. However, the above proposed methods require the examining staff to patrol houses having termite-detectors set to visually check the detectors. The houses with the detector would be scattered in wide ranges, so that the check requires a great deal of time and expense.

In addition, as wooden pieces were used as a material for inducing termites in the conventional arts, such materials are naturally expected to be the same with the wooden building material for a house under test. As a result, even if such materials were used as the detecting samples for inducing termites, it might be considered in a great possible extent that the termites would selectively prefer eating the wooden building materials constituting that house.

Further, as to the aforementioned methods of detecting termites by visually observing the existence of termites in the wood, etc., set on invading passages or by checking, at every time, whether or not wood is damaged by any wood-eating insects using supersonic non-destructive tester, etc.; the present state is that no low-cost sensor for such a detection has been developed yet which allows the system to monitor the house under test around the clock throughout the year.

There is another method in which sounds caused when wood is damaged by termites and transmitted through the wood are measured by using the conventional A.E. sensor and the like. However, in this method, the sounds are picked up from the wood surface through the air with a microphone so that it is impossible to obtain clear sounds. Further, depending upon the situations of the microphone being attached, only particular noises through the air might be picked up so that no one except well-skilled operators can distinguish the wood eating sounds from the noises. Similarly, the aforementioned analyzing means of vibratory waveforms may be considered to require experienced, well-skilled operators.

Moreover, a lot of sensors being placed under floors is hard to find when the inspection is to be carried out.

SUMMARY OF THE INVENTION

It is therefore an object of the present invention to find out invasion of termites in an early stage, without waiting swarming of termites, as soon as termites enter a house and are attracted by a termite sensor disposed in an expected invading passage or as soon as termites start to eat and damage a detecting sample in a termite sensor disposed in the same way.

It is another object of the present invention to provide a system which, without requiring inspecting staff to patrol a number of houses over a wide area, can integrally collect inspected result of damages caused by termites as to the houses.

In order to achieve the above objects of the present invention, the present invention is constructed as follows.

In accordance with an aspect of the invention, a termite detecting device is placed in an expected invading passage for detecting damage or destruction caused by termites, and comprises: a detecting sample for attracting termites; a detecting terminal being pressed against the detecting sample for transmitting displacement or vibrations due to the damage or destruction caused by termites; and an elastic member for pressing the detecting terminal or the detecting sample. The termite detecting device further comprises any one of a moving structure being attached with the detecting terminal and capable of moving by virtue of elastic pressing force generated by the elastic member, or a vibration sensor for detecting vibrations transmitted from the detecting terminal, whereby detection of termites is carried out based on the detection signal obtained from any one of the moving structure and the vibration sensor.

In this configuration, it is effective that the detecting device further comprises a fixed member made from a magnetic substance, a permanent magnet and a magnetic sensor, and that the moving structure comprises the magnetic substance while the moving structure, the fixed member and the magnetic member constitute a magnetic circuit and the magnetic sensor is arranged in a gap of the magnetic path. Alternatively, it is further effective that the magnetic substance has a high permeability and a low remanence.

Next, in accordance with another configuration of the present invention, a termite detecting device is placed in an expected invading passage for detecting damage or destruction caused by termites, and comprises: a detecting wood sample for attracting termites; a detecting terminal being pressed against the detecting wood sample for transmitting displacement due to the damage or destruction caused by termites; and an elastic member for pressing the detecting terminal; a magnetic circuit capable of being opened or closed by the movement of the detecting terminal so as to generate a detection signal indicating detection of termites; and a water supplying means for supplying a proper amount of water to the detecting wood sample.

In this case, it is effective that a constant amount of water is supplied at regular intervals preferably from a water reservoir tank. Alternatively, it is also effective that supplied water uses rainwater or dew condensation water.

In the above-described main two configurations, any of the following features is effective. That is, the detecting terminal has a tip potion shaped in a dome-like or spike-like form and a barrel portion having a small contact area equivalent to that of the tip and presenting a small sinking resistance; the wood piece used as the detecting sample is set and buried in earth and sand which fills up inside an enclosed wall provided in the periphery of a casing of the detecting device body; the wood piece used as the detecting sample is arranged such that the detecting terminal presses the wood piece in a direction substantially perpendicular to the layers of annual rings of the wood piece; the wood piece used as the detecting sample is provided with slits; all the components constituting the magnetic circuit is hermetically separated from the portion that accommodates the detecting sample; and the device body containing all the components constituting the magnetic circuit is covered by a magnetic shield.

In accordance with a further aspect of the present invention, a termite detecting device is placed in an expected invading passage for detecting collection or aggregation of termites, and comprises: an attractant for attracting termites; a detecting terminal for guiding termites to a holding tray for the attractant; and a vibration sensor for detecting vibrations of the detecting terminal accompanied by the collection and movement of termites and generating a detection signal.

In the above-described main three configurations, any of the following features is effective. That is, clearances for allowing termites to go in and out freely are provided everywhere on a casing of the detecting device body in the form of openings whose size is substantially equal to or in correspondence with the dimension of a termite; a termite-guiding pheromone is used solely or combined with the detecting sample, in order to attract termites; the outside surface of a casing of the detecting device body is affixed with a light-reflecting member serving as an identifying marker; and the termite detecting device further comprises a data transmitting system whereby the detection signal is terminal-transmitted from the detecting device to an external, central control center apparatus by way of telephone line and is integrally controlled by the central control center apparatus.

Furthermore, in the present invention, by using the thus constructed termite detecting device, it is possible to provide novel methods of detecting termites and the features of the methods will be followed.

That is, a first feature of the method of detecting termites, uses a termite detecting device comprising: a wood piece as a detecting sample for attracting termites; a magnetic circuit being composed of, at least, a magnetic substance member as a moving portion and a permanent magnet; a magnetic sensor disposed in a gap of the magnetic path of the magnetic circuit; and a detecting terminal being attached to the moving portion, and abutting and pressing the wood piece in a direction substantially perpendicular to the layers of annual rings of the wood piece with the help of an elastic member, and is characterized in that, when the wood piece is eaten and hollowed by termites to become fragile, the detecting terminal sinks into the wood piece thereby shifting the moving portion; the movement of the moving portion opens or shuts down the magnetic circuit; and the magnetic sensor detects the shutdown of the magnetic circuit and issues a valid signal which is in turn terminal-transmitted through telephone line to a certain place so as to be integrally controlled.

In this case, it is effective that the wood piece is pressed by the detecting terminal while being supplied with a proper amount of water.

A second feature of the method of detecting termites, uses a termite detecting device comprising: a wood piece or a termite-attractant held in a attractant-holding tray as a detecting sample for attracting termites; a vibration sensor; and a detecting terminal being connected to the vibration sensor, and being pressed and abutted against the 10 wood piece or being hanged down to the vicinity of the bottom of the detecting device, passing through the attractant-holding tray, and is characterized in that, when termites start to eat the wood piece or when termites are attracted by the attractant and start to climb up along the detecting terminal to collect on an upper portion of the device, the vibration sensor picks up the vibrations generated by either phenomenon and issues a valid signal which is in turn terminal-transmitted through telephone line to a certain place so as to be integrally controlled.

The present invention is thus configurated. Accordingly, when a wood piece, for example, is used as a detecting sample, the termite detecting device is set on an expected invading passage in such a manner that the detecting sample is buried partly or wholly in the earth. When termites invade and start eating, the detecting sample is gradually hollowed out. As the cavitation advances, the detecting terminal that presses the detecting sample with a predetermined pressure, gradually or abruptly, sinks into the detecting sample. The movement of the detecting terminal causes the magnetic path of the magnetic circuit to be opened or shut down. As a result, the magnetic sensor which has sensed constant magnetic fields provided by the magneto motive force of the permanent magnet, changes its output from ON-state to OFF-state. In response to the sensor signal, an indicator disposed in a house is activated to warn. Alternatively, the observation is achieved around the clock and the result can be transmitted to the control center by using telephone line and the like. In this way, it possible to take a quick action for exterminating measure.

In the present invention, since the detecting wood sample for attracting termites is supplied with a proper amount of water, this configuration presents an excellent effect on attracting termites as compared to a normal conventional case in which a dry wood sample is used. As a result, it is possible to attract termites selectively to the detecting wood sample. In other word, by taking advantage of inclination of termites to willingly eat damp wood, such a simple method as supplying water, makes it possible to detect termites markedly effectively in a reliable manner.

Further, in the present invention, since the wood sample or termite-attractant is used together with the termite detecting means including the vibration sensor, neither will the detection be influenced by the species of wood nor by the damaged state of wood and the like. In sum, vibrations accompanied by termites starting to eat wood or by termites gathering may be monitored as a detection signal.

In addition, by affixing a light-reflective member as an identifying marker on the outside of the casing of the detecting device body, it is possible to readily locate the device set in dark places such as an underfloor site with a portable lamp, etc., whereby the inspecting work may be achieved markedly efficiently.

In connection with the means for supplying water, the following experiment was carried out. That is, of the termites inhabiting Japan, namely, Yamato-Shiroari and Ie-Shiroari, the former termites were used for the experiment in order to make sure the inclination to willingly eat damp wood.

Initially, FIGS. 1A and 1B show a colony container for breeding source of termites, and FIG. 1A is a front section showing an overall illustration of the colony container and FIG. 1B is a perspective view thereof. FIG. 2 is a front section showing an overall illustration of a testing vessel holding a colony container shown in FIGS. 1A and 1B for making a comparison of the effect on attracting termites in different conditions of supplying water to wood. FIG. 3 is a schematic diagram showing setup conditions of the above comparing test.

First, as shown in FIGS. 1A and 1B, a wood piece 22 inhabited by 100 worker termites as well as damp sand 25 was placed in a colony container 18 having vents 21. A gateway 20 was disposed at a center on the top board of colony container 18 for allowing termites to go in and out. As a footing for termites, a thin footing piece 19 was planted on the sand through gateway 20. This was the only escape. Next, as shown in FIG. 2, colony container 18 was placed on the bottom of a testing vessel 30 in a center portion thereof while all the part of container 18 except the top face thereof having gateway 20 was buried with sand 25. A pair of wood blocks 24 were placed symmetrically with an equal distance kept from the center of gateway 20 for termites. A water container 23 for supping water was placed on a wood block 24 and water was supplied through a filter paper 26.

Here, testing vessel 30 was accommodated by an outer box 31 and covered by a lid 32 so as not to permit termites to go outside.

Testing conditions were set up as follows.

Setup 1) only one of the wood blocks was supplied with water.

Setup 2) Neither of the two wood blocks was supplied with water.

Testing wood sample: pine wood (which is most preferred as foods by termites)

Evaluation method: three observations were carried out after one day, three days and seven days, respectively. The number of termites gathered in each test section was counted.

Result: From the result of test setup 1, it was confirmed that termites selectively gathered to the test section supplied with water. As shown in Table 1, after three days from the start of the test, 70 termites out of the whole tested group gathered to the water-supplied section. In contrast, as shown in Table 2, no termite was observed to move to the wood blocks in test setup 2.

TABLE 1

(Setup 1)

| Moving individual identified site | | One day after (I.N.)*1 | Three days after (I.N.) | Seven days after (I.N.) |
|---|---|---|---|---|
| Wood blocks | A: Water supplied | 21 | 70 | 38 |
| | B: No water | 0 | 1 | 0 |
| Other site*2 | | 5 | 2 | 0 |

*1: abbreviation of individual number
*2: outside the colony container

TABLE 2

(Setup 2)

| Moving individual identified site | | One day after (I.N.)*1 | Three days after (I.N.) | Seven days after (I.N.) |
|---|---|---|---|---|
| Wood blocks | A: Water supplied | 0 | 0 | 0 |
| | B: No water | 0 | 0 | 0 |
| Other site*2 | | 0 | 0 | 0 |

*1: abbreviation of individual number
*2: outside the colony container

From the experiment result above, it is apparent that the wood piece supplied with water exhibits a selective effect on attracting termites.

BRIEF DESCRIPTION OF THE DRAWINGS

FIG. 1A is a front section showing an overall illustration of a colony container for use in an experiment confirming inclination of termites;

FIG. 1B is a perspective view of the colony shown in FIG. 1A;

FIG. 2 is a front section showing an overall illustration of a testing vessel;

FIG. 3 is a schematic diagram showing setup conditions for a comparing test;

FIG. 15 is a block diagram showing a schematic configuration of a circuit for a terminal net control unit connected with an external station for use in a termite detecting device of the present invention.

DESCRIPTION OF THE PREFERRED EMBODIMENTS

Illustrated embodiments of the present invention will hereinafter be described with reference to the accompanying drawings.

Figure 4:
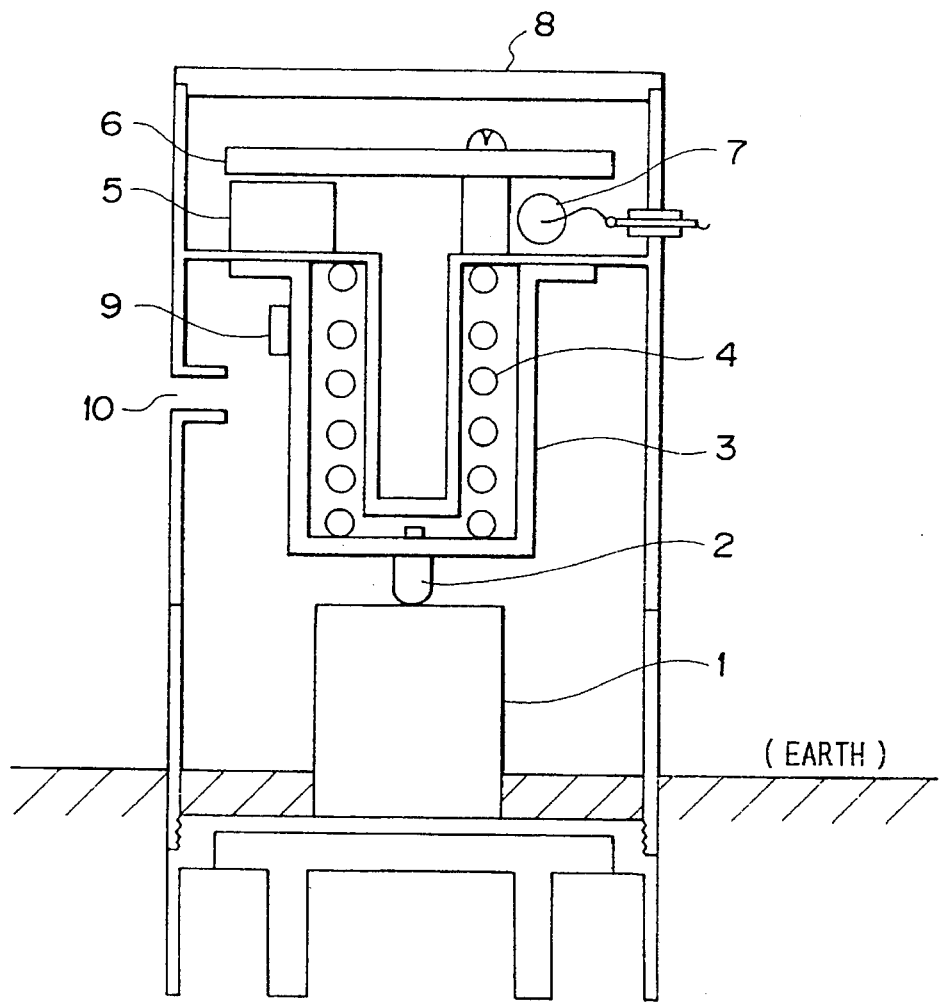
FIG. 4 is an overall sectional view showing an embodiment of a termite detecting device of the present invention.

First of all, FIG. 4 is an overall sectional view showing an embodiment of a termite detecting device of the present invention. Reference numeral 1 designates a detecting sample made from pine, cedar or wooden material for attracting termites. A detecting terminal 2 is abutted by a predetermined pressure against one side of the detecting sample 1. This pressing force is caused by an elastic material 4 such as a spring, or the like which compressing a moving structure 3 to which detecting terminal 2 is attached. The other side of detecting sample 1 abuts the bottom face of a case 8 which supports the pressing force acted on detecting sample 1. Moving structure 3 is made from a magnetic substance such as metals and the like, and forms a magnetic circuit together with a fixed structure 6 made of a magnetic substance and affixed to case 8, and a permanent magnet 5 producing magneto motive force and attached to moving structure 3 or fixed structure 6. A magnetic sensor 7 is disposed at a gap of the magnetic path. Further, the moving structure 3 has a red mark 9 attached thereto and as moving structure 3 is moved, the movement of red mark 9 can be visually observed from the outside through an opening portion, indicator window 10 provided on the side of case 8.

Figure 5:
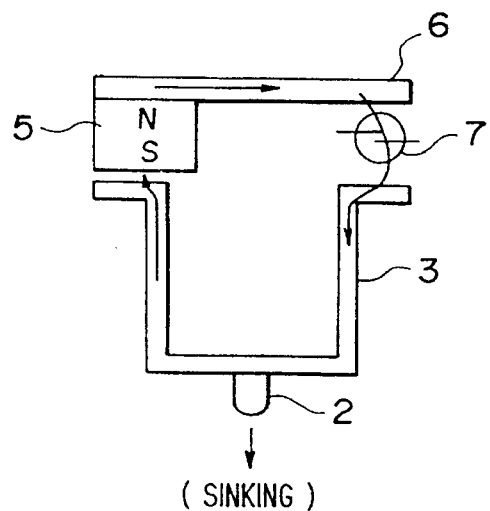
FIG. 5 is a view showing the operation of essential components relating to a magnetic circuit of the termite detecting device shown in FIG. 4.

Next, FIG. 5 is a view showing the operation of essential components relating to the magnetic circuit of the termite detecting device in the above embodiment of the present invention. When the device is mounted at the beginning, detecting terminal 2 does not sink into detecting sample 1 while the magnetic circuit formed of moving structure 3 of magnetic substance, fixed structure 6 and permanent magnet 5 is in a closed loop state. In this situation, when a reed switch is used as the magnetic sensor 7 securely supported by case 8 and positioned at the gap of the magnetic path, the reed switch is being in a conductive state due to the magnetism.

As termites invade into detecting sample 1 while eating it to be hollow, detecting terminal 2 gradually or abruptly sinks into detecting sample 1. This fall causes moving structure 3 to move so as to make the magnetic circuit open. Accordingly, the magnetic path is opened or shut down so that the magnetic fluxes reduce suddenly to thereby bring the reed switch positioned at the gap of the magnetic path to a non-conductive state. At the same time, red mark 9 moves to indicate through indicator window 10 that detecting terminal 2 has sunk into the wooden sample.

Since the detecting device of the present invention is placed at an expected position as an intruding path of termites, the device need work over a long period of time. That is, it will take at least some years after the mounting until any eaten damage of termites is detected. Accordingly, in order to operate the sensor without failure over a long period of time, a conductor Hall element may be used as the magnetic sensor as well as a reed switch that has a contact portion sealed. Further, in order to make the device operate without fail or to prevent misoperation of the device even when iron sands and any other pieces of iron scraps are attracted to the magnetic circuit for some causes, the magnetic circuit is adapted to be opened or shut down when detecting terminal 2 sinks down. Moreover, if a signal line of magnetic sensor 7 is broken by rats or the like to be opened, the opened state of the device can be taken as a valid signal to indicate and alarm the abnormality.

Further, the leading end of detecting terminal 2 is shaped in dome-like or spike-like form so that the pressing force concentrates on detecting sample 1 to make detecting terminal 2 sink easily, facilitating moving structure 3 to move.

Since termites prefer to feed and destroy the wood and the like being in the earth, the embodied detecting device for termites of the present invention is buried partly in the earth. Specifically, the opened bottom of case 8 is in touch with the earth and detecting sample 1 placed at the bottom is buried partly or wholly in the earth.

Here, although no particular depiction is made, it is effective to provide around the surface of the earth a lot of openings or slits everywhere having a dimension corresponding to about the size of termites so as to allow termites to go in and out freely.

Next, a second embodiment of the present invention will be described with reference to the drawings.

Figure 6:
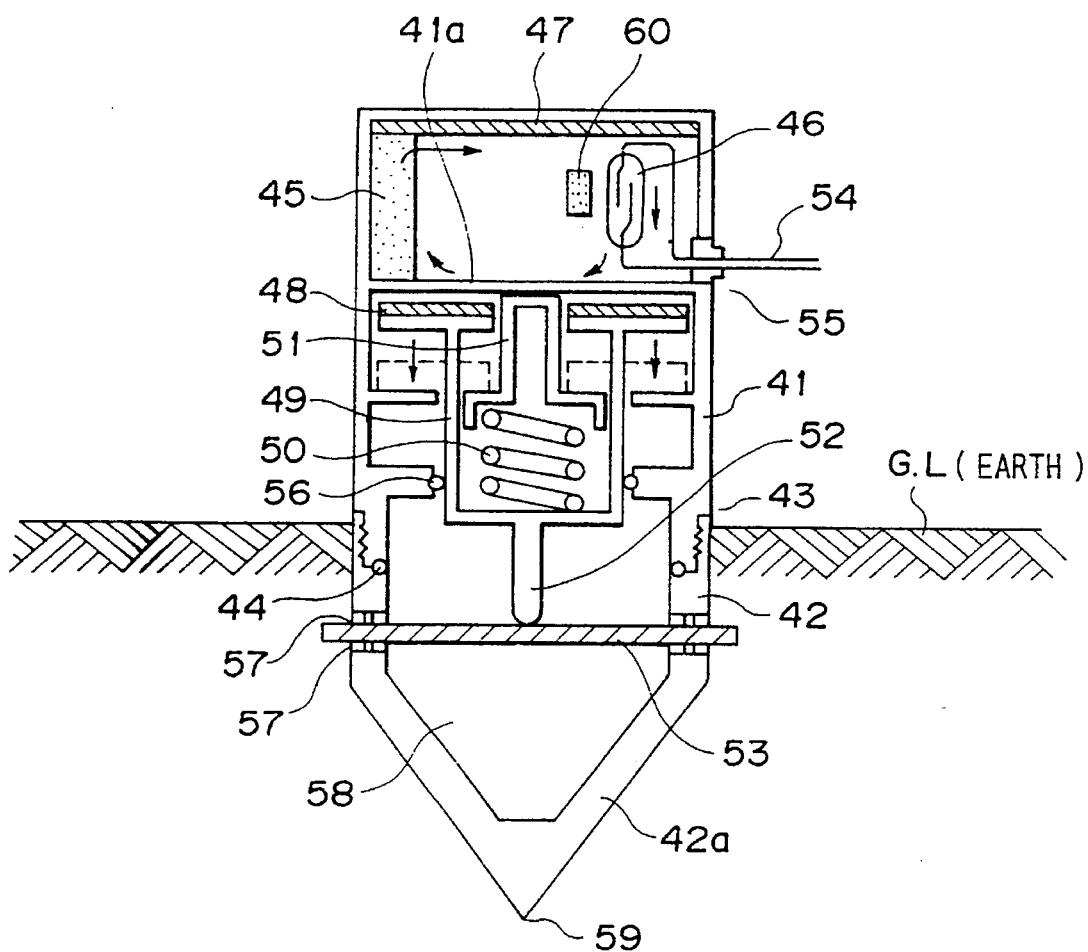
FIG. 6 is a vertical sectional view of main components showing a configuration of a termite detecting device of a second embodiment of the present invention.

FIG. 6 is a vertical sectional view of main components showing a configuration of a termite detecting device of the second embodiment of the present invention. Reference numeral 41 designates an upper case having a magnetic circuit therein. This upper case 41 is preferably made from a plastic which is hard to be damaged by termites and has a prolonged stability. Designated at 42 is a lower case which accommodates a wooden member for detection and which is integrally united with upper case 41 by screw fitting. The screw fitting portion designated at 43 has an O-ring 44 therein which prevents muddy water, etc., from entering through screw fitting portion 43.

Upper case 41 incorporating a magnetic circuit will be described on its overall configuration.

Reference numerals 45 and 46 designate a permanent magnet made of ferrite, etc., and a reed switch, respectively.

Numeral 47 designates a fixed magnetic substance member which serves as a part of the magnetic circuit and is made from a material having a large magnetic permeability and a less remanence such as 52-alloy (an alloy containing a 52% of nickel and a 48% of iron) and the like. Reference numeral 48 is a moving magnetic substance member which is made from the same material with the fixed magnetic substance member and which is integrated with a movable shaft 49. Provided inside movable shaft 49 is an elastic member 50 which is fit into a holding portion 51. Movable shaft 49 is provided at a lower part thereof with a detecting terminal 52, which in turn presses at its tip against wooden detecting member 53.

Unless wooden detecting member 53 is placed, movable shaft 49, urged by elastic member 50, is being pushed down to a level shown by the broken line while holding portion 51, abutting at its upper portion against a partitioning plate 41a of the case, stays fixed.

When wooden detecting member 53 is placed, movable shaft 49 is pushed upward so that moving magnetic substance member 48 is positioned up to proximity with partitioning plate 41a. As a result, a closed magnetic circuit consisting of permanent magnet 45, fixed magnetic substance member 47, reed switch 46 and moving magnetic substance member 48 is formed. In this situation, if reed switch 46 is made of A-type contact, the contact stays in a closed state so as to supply ON-output through a signal line 54 extracted from reed switch 46.

A bushing 55 is provided at the exit of signal line 54 for the purpose of water protection.

If wooden detecting member 53 is eaten by termites and therefore the strength is lowered causing destruction of the wood, detecting terminal 52 as well as movable shaft 49 is pressed down by elastic member 50. Moving magnetic substance member 48 integrated with moving shaft 49 also downs to the level shown by the broken line so that a space is created between permanent magnet 45 and moving magnetic substance member 48. As a result, the magnetic circuit is opened so that the contact of reed switch 46 becomes open so to deliver OFF-output through signal line 54.

An O-ring 56 for sealing is provided at the engaging portion between the aforementioned case 41 and movable shaft 49 in order to prevent dusts and water, etc., from entering the space in which moving magnetic substance member 48 is accommodated. By filling up the hermetic space with an inert gas, it is possible to provide a stable performance for the device over a long period of time.

Wooden detecting member 53 is held at its fitting portion by lower case 42 with clearances 57 of about 3 mm being kept. Termites have the taxis for channel and start eating from a contact portion or a butt joint between wood, so that it is effective to provide clearances in the fitting portion between lower case 42 and wooden detecting member 53 in order to attract termites.

A space 58 is provided in lower case 42 under wooden detecting member 53, and if it is necessary to attract termites strongly, an attractant such as guiding pheromones, etc., can be put in the space 58.

Since habitat centers of termites exist mostly in the soil in which temperature as well as humidity is stable, the detecting device of the present invention should be mounted so that wooden detecting member 53 may be set under the surface of the earth. In order to facilitate the device to be buried, the lowermost part of lower case 42 is preferably formed with a projection 42a (having a cone-shaped tip 59), but the shape is not limited to this and can be formed with a flat surface depending upon mounting situations.

A reference numeral 60 in FIG. 6 designates a bias magnet. This is required in the case where a B-type reed switch is used as a contact for output. It is also possible to form a similar contact by using a C-type reed switch. In the case of B-type reed switch being used, the output to signal line 54 stays OFF while wooden detecting member 53 has not yet been eaten. Accordingly, this configuration gives an advantage in saving power consumption. A further advantage is that, if many sensors are set and all the outputs are supplied to a single control unit, the sensors may be connected simply in parallel.

Figure 7:
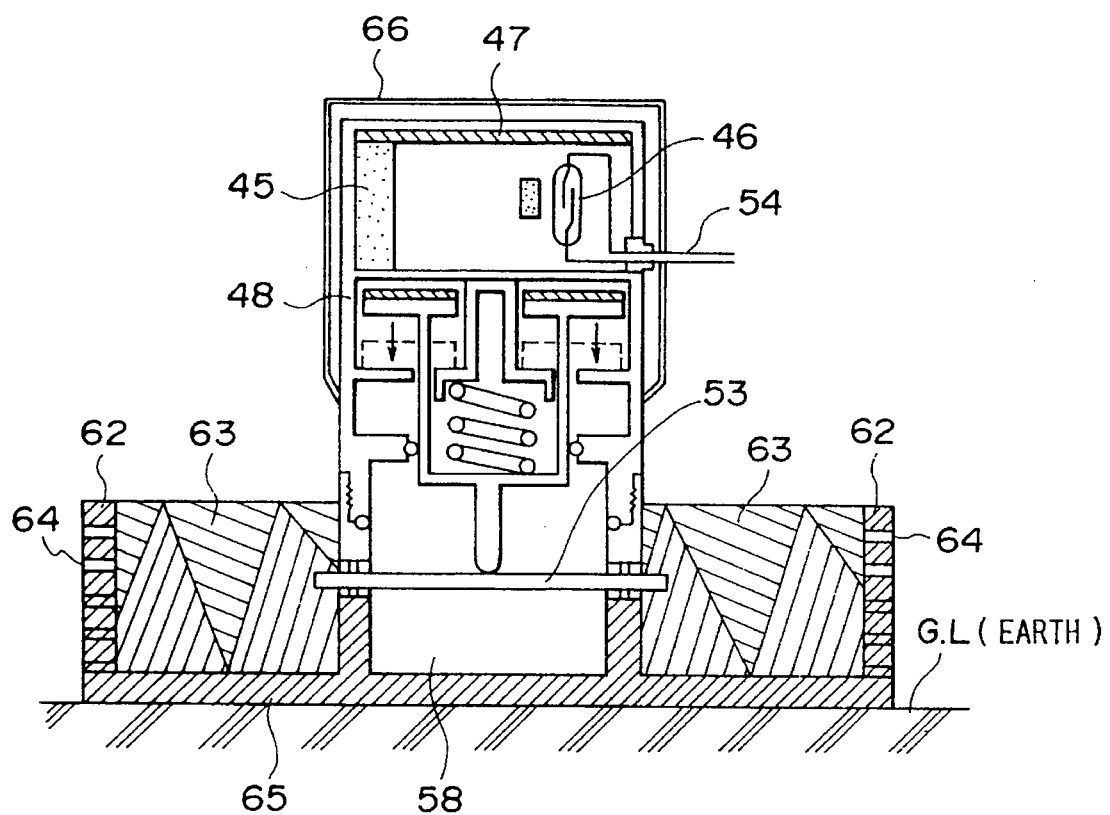
FIG. 7 is a view showing a variation of the detecting device shown in FIG. 6.

FIG. 7 shows another variation of the above embodiment. This configuration including its magnetic circuit and wooden detecting member 53 and other elements are almost the same with that shown in FIG. 6. A main difference of the configuration shown in FIG. 7 from that in FIG. 6 is that, if the earth surface is concreted under the floor or no earth surface is exposed, this structure allows termites to easily be attracted.

Therefore, the description of the embodiment will be made with only the different points.

A lower case 65 is flat-shaped in its bottom with an enclosing wall 62 disposed in the periphery. Earth and sand 63 are put into the gutter defined between case 65 and enclosing wall 62 in order to attract termites readily. A large number of passing holes 64 are provided on enclosing wall 62 in order to allow termites to enter the device with ease. No passing hole 64 is provided on the bottom so that water supplied to the earth and sand 63 at the time of mounting is prevented from leaking out. By the structure, the termites having invaded into the house can be easily attracted to the detecting device of the present invention, and consequently, it is possible to find out the invasion of termites in its early stage and therefore to cope with them.

As a variation of the embodiment, a magnetic shield member designated at 66 in FIG. 7 can be provided in order to protect the internal magnetic circuit from being affected by external magnetic fields.

Figure 8:
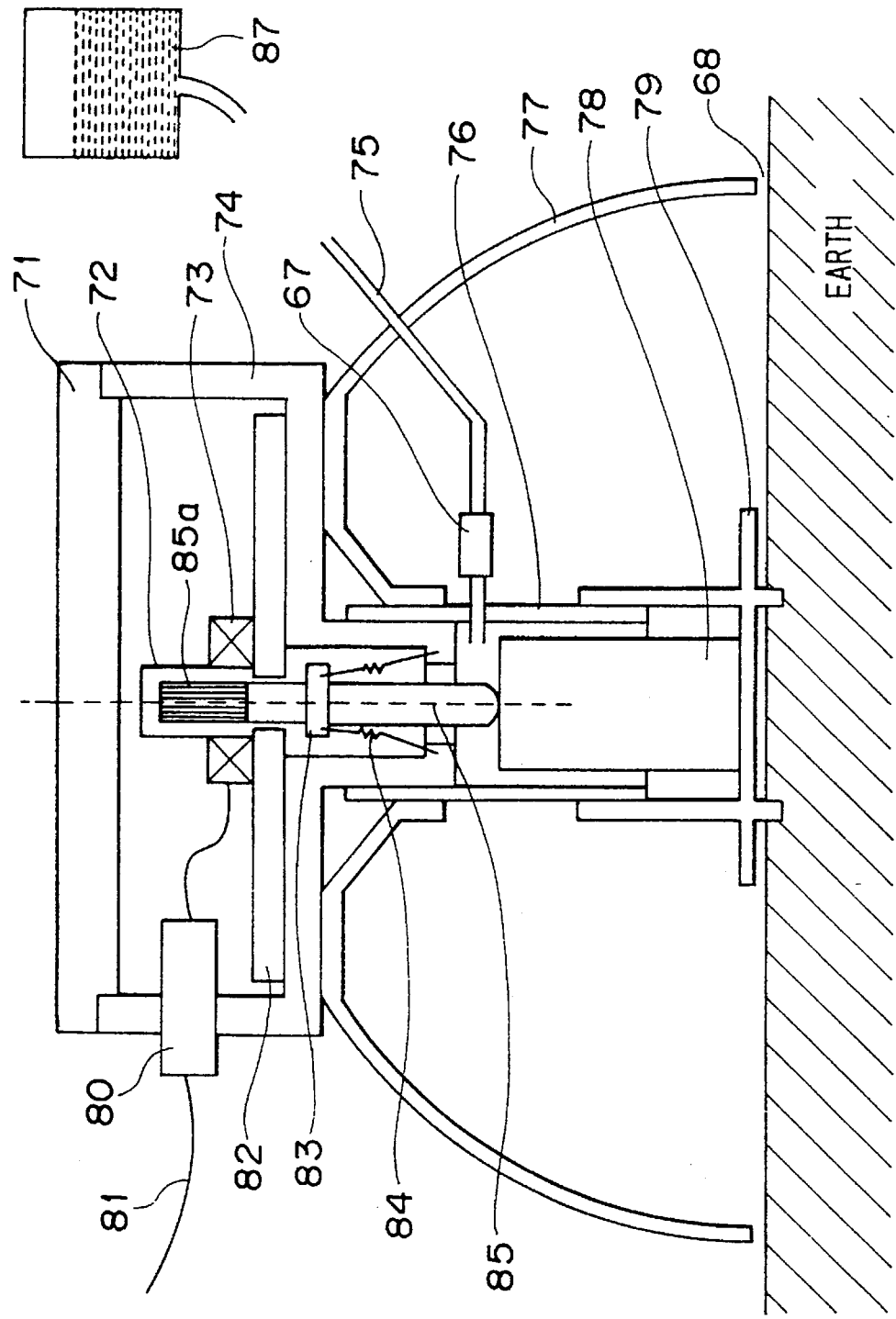
FIG. 8 is an overall vertical front sectional view showing a configuration of a termite detecting device of a third embodiment of the present invention.
Figure 9:
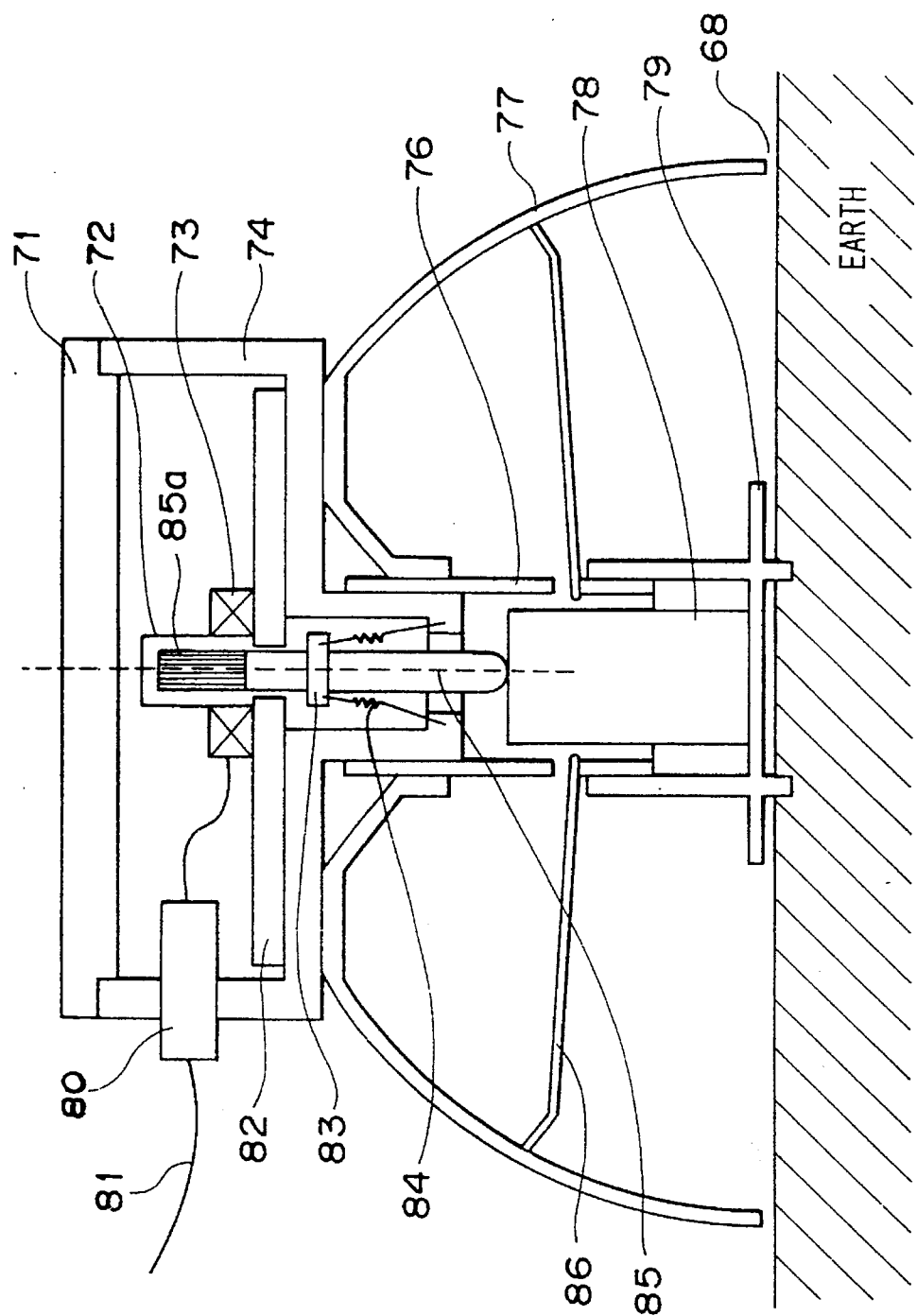
FIG. 9 is a view showing a variation of the detecting device shown in FIG. 8.

Next, a third embodiment of the present invention will be described with reference to the drawings. FIGS. 8 and 9 are schematically illustrated front sectional views each showing a different variation of a termite detecting device of a third embodiment of the present invention.

Hereinafter, the basic configuration of the termite detecting device of this embodiment will be described referring to FIGS. 8 and 9. In these figures, reference numerals 78 and 85 designate a wooden detecting sample and a detecting terminal, respectively. Designated at 73 is a proximity sensor of reed switch type. An uppermost portion 85a of detecting terminal 85 is made up of a metal and enclosed by a cover 72, forming a magnetic circuit with the aforementioned proximity sensor 73. This proximity sensor 73 is attached onto a sensor attachment plate 82 accommodated by a sensor case body 74 covered with a case lid 71, and is connected to a sensor cable 81 which in turn is connected passing through a rubber bushing 80 with a predetermined control center and the like so that the pickup signal can be transmitted thereto.

The sensor case body 74 is supported by a supporting cylinder 76 which in turn mounted on a sensor supporting base 79. This sensor supporting base 79 is set on the earth surface and also serves to accommodate the aforementioned detecting wood sample. On the other hand, an elastic member attaching plate 83 is provided around the middle portion of the detecting terminal 85. Further, a pressing elastic member 84 such as, for example, a spring, is provided between the sensor case body 74 and the elastic member attaching plate 83 so as to force the detecting terminal 85 downward or to urge the detecting terminal 85 to press the surface of detecting wood sample at any time.

Reference numeral 77 designates a sensor cover, and in order to assure passages allowing termites to enter the detecting device of the embodiment of the present invention, a clearance 68 is provided between sensor cover 77 and the earth surface.

As described above, the termite detecting device of the embodiment of the present invention is basically thus constructed. Further, in this embodiment, a means for supplying an appropriate amount of water to the detecting wood sample 78 is provided for the thus formed configuration. This serves to remarkably enhance the effect on attracting termites. That is, it is apparent from the experiment result set forth above that termites have inclination to willingly eat wood with moisture. In this case, as to the moisture supply, periodically supplying of water in a constant amount is most effective. As a means for supplying moisture, it is effective to use a regulating valve 67 as shown in FIG. 8 which is controlled by an arbitrary controller in order to deliver water from an unillustrated water source through a water-supply pump 75.

In this case, the means for supplying water may use a water reserving tank 87. As to water to be supplied, typical city water, ground water, or the like can be utilized. Other than these water sources, rainwater may also be used, and this may economize the water supply.

FIG. 9 shows a variational example of the embodiment in which dew condensation water is used as the supplying water. In FIG. 9, designated at 86 is a tray for collecting dew condensation. In this case, the aforementioned sensor cover 77 need particularly be made from a metal in order to condense water on the inner wall of the cover 77 utilizing the temperature difference between the inner wall and outer wall of the cover 77 or the temperature difference between day and night. Thus obtained dew condensation water is collected by dew collecting tray 86 to supply it to detecting wood sample 78.

In this case, it is naturally suspected that, depending upon seasons, no significant temperature difference can occur between the inner wall and outer wall of sensor cover 77. To deal with such a case, an unillustrated heater may be provided inside sensor cover 77 to generate temperature difference.

Besides, since sensor cover 77 is made from a metal and therefore is naturally opaque, it is possible to prevent light from entering the inside of sensor cover 77. This feature, in corporation with supplying water, may create a more desirable environment for termites that prefer dark places. As a result it is possible to further enhance the desired effect of the sensor.

Next, the operation of the termite detecting device of the embodiment of the present invention will be described with reference to the drawings. To be simple, the configuration shown in FIG. 8 is mainly described at first. Initially, a place to be expected as an intruding passage of termites such as a underfloor site, etc., is selected in a house under test. Then sensor supporting base 79 is set on the earth in the selected site. Next, a detecting wood sample 78 is put into the base. In this case, it is effective to use a detecting wood sample 78 having slits 103 formed on the surface thereof. This will be described in detail later. Then, case body 74 with detecting terminal 85 that is urged by pressing elastic member 84 is mounted through supporting cylinder 76 to the aforementioned sensor supporting base 79. In this case, it is convenient that sensor cover 77 is integrally formed on any side of case body 74 and supporting cylinder 76.

In this way, as the device is set so that the tip of detecting terminal 85 presses the surface of detecting wood sample 78, the metallic, uppermost portion 85a of detecting terminal 85 in cooperation with proximity sensor 73 creates a closed magnetic circuit.

In this arrangement, with respect to the configuration shown in FIG. 8, the water being delivered through water supplying pipe 75 from water reservoir tank 87 holding city water, ground water, or rain water, is controlled by regulating valve 67 so as to periodically supply a constant amount of water to detecting wood sample 78. Alternatively, with respect to the configuration shown in FIG. 9, water that has been condensed on the inner wall of sensor cover 77 and collected by dew collecting tray 86 is supplied to detecting wood sample 78. In either way, it is possible to keep the detecting wood sample 78 at any time in a well-moist state which may effectively attract termites.

In this case, the interval and the amount of supplying water may be determined optimally case by case based on the humidities and temperatures of atmospheres inside and outside sensor cover 77 as well as the dimension and shape of the detecting wood sample 78 and the width, depth and the number of slits if slits 103 are provided.

As preparation is thus made, suppose that any termites invade the device, the termites enter the sensor through clearance 68 disposed between sensor cover 77 and the earth surface to selectively eat the detecting wood sample 78 containing moisture. As a result, the termites eat and destroy wood sample 78 by starting, in particular, the soft, spring wood portion in wood sample 78 to hollow out the inside of the wood, making the wood sample 78 fragile.

As a result, the tip of detecting terminal 85 being urged by pressing elastic member 84 sinks into detecting wood sample 78 and therefore detecting terminal 85 moves downward. With this movement, metallic uppermost portion 85a of the detecting terminal drops to thereby open the magnetic circuit formed by proximity sensor 73 and the portion 85a itself. Accordingly, the contact of the reed switch changes its state from ON-state to OFF-state. The thus generated signal is transmitted via sensor cable 81 to a predetermined control center and warns the staff of the termite invasion. In this way, it is possible to find the invasion of termites in its early stage. Afterwards, any required measure will be taken rapidly such as contacting with a termite-exterminating trader so as to make them sterilize the house to stamp out termites.

Figure 10:
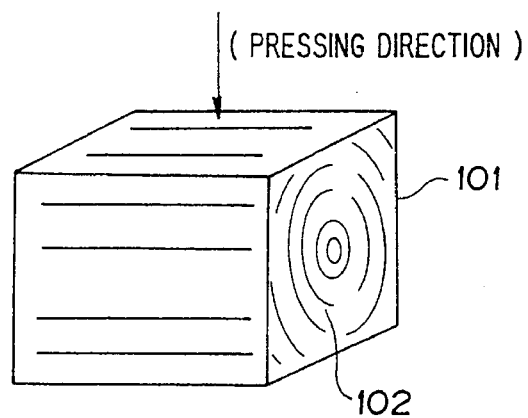
FIG. 10 is a perspective view showing an example of the feature of a detecting wood sample for use in an embodiment of the present invention.
Figure 11:
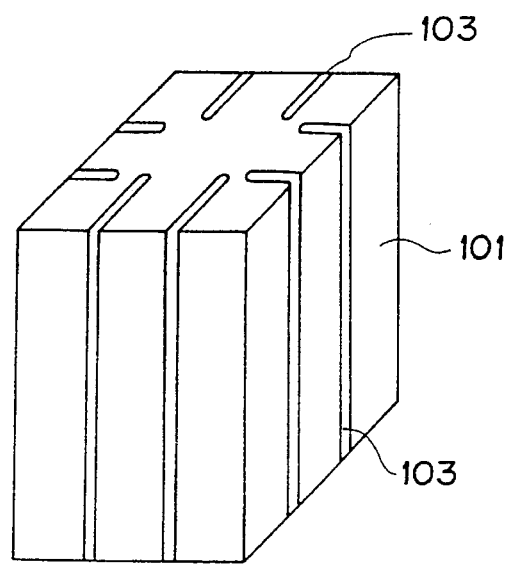
FIG. 11 is a perspective view showing another example of the feature of a detecting wood sample for use in an embodiment of the present invention.
Figure 12:
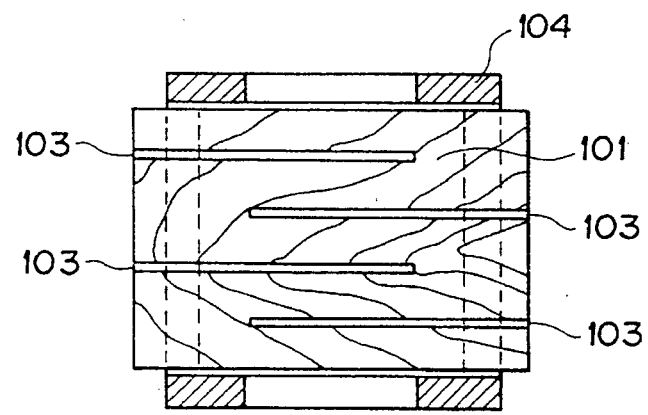
FIG. 12 is a plan view showing an example of the feature of a plate-like detecting wood sample for use in an embodiment of the present invention.

Now, the detecting wood sample used in the embodiments of the present invention will be described as to its shape and feature with reference to the drawings. FIGS. 10 to 12 are views for illustrating the shapes and features.

In these figures, reference numerals 101, 102 and 103 designate a wood sample, an annual ring and a slit, respectively.

First of all, consider the sampling and setting of wood sample 101. As general requirements, in order to surely detect cavitation eaten by termites, a termite-preferred wood such as, in particular, pine, cedar and the like should be selected as the sample material. The thus selected wood is cut and taken so as to be pressed by the detecting terminal in a direction, as perspectively shown in FIG. 10, perpendicular to layers of annual rings 102, in stead of pressing the layers of annual rings 102 in a parallel direction. The reason is that termites in general have inclination to willingly eat layers of soft, spring wood portion along annual rings 102, leaving layers of hard, autumn wood portion so that the hollowed wood is fragile to a force perpendicular to the layers of annual rings.

Further, since termites present the taxis for channel as described previously and therefore they are attracted to clearance portions in the wood, the destruction by termites is easy to start from the clearance portions. Hence, it is effective to create a plurality of narrow slits 103 near the surface of the detecting wood sample 101 used in the present invention as perspectively shown in FIG. 11. A preferable width of such slits is from about 2 to 3 mm. When the thus shaped detecting wood sample 101 is supplied with water as the aforementioned third embodiment, the supplied water, entering the slits 103, is absorbed easily and rapidly by wood sample 101 up to the deeper inside thereof, presenting a further increased effect on attracting termites.

Next, FIG. 12 is a plan view showing a plate-like detecting wood sample 101 to be preferably used in the second embodiment set forth above. An optimum material for the detecting wood sample 101 is pine that is most preferred by termites. In this figure, reference numeral 104 designates a lower case of the device.

As described previously, termites start to eat soft, spring wood portion along annual rings of the wood, leaving hard, autumn wood portion, so that the remnants of wood take a lamella structure in parallel with cross-grained face of wood. Therefore, strength normal to the cross-grain face of the wood lowers sharply. Therefore, the detecting wood sample 101 uses a cross-grained board while the board is provided with slits 103 of about 3 mm wide for taking advantage of the channel-taxis of termites. The provision of these slits 103 is one of most important feature of the present invention since slits 103 not only attract termites but also cause the strength of wood against the pressing force of the detecting terminal to lower sharply when the detecting wood sample 101 is eaten by termites, thereby enabling assured detection of termites in an earlier stage.

Figure 13:
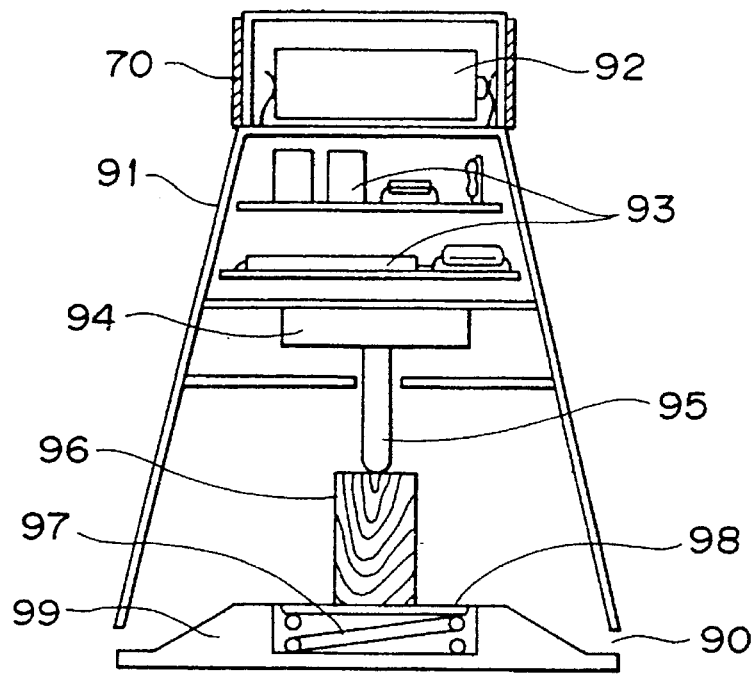
FIG. 13 is an overall vertical front sectional view showing a configuration of a termite detecting device of a fourth embodiment of the present invention.
Figure 14:
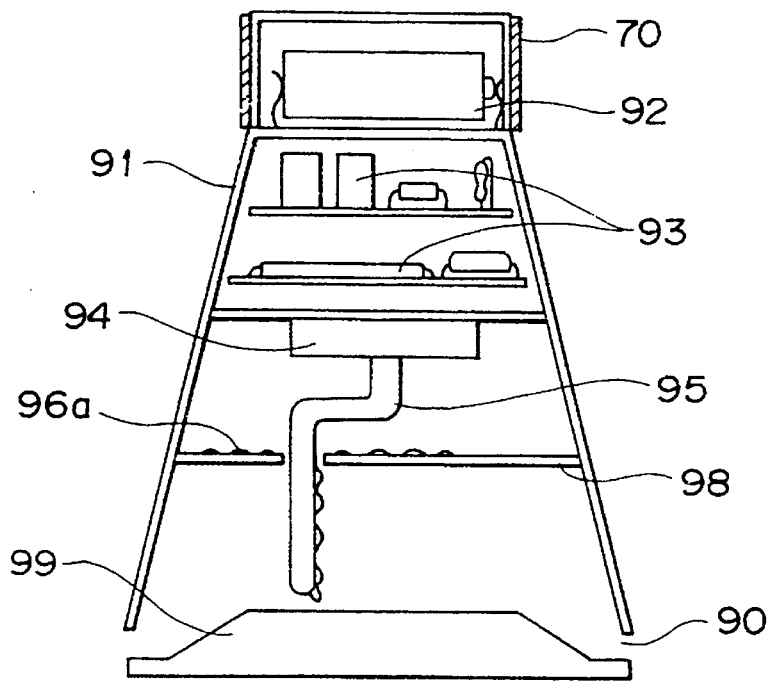
FIG. 14 is a view showing a variation of the detecting device shown in FIG. 13.

Finally, a fourth embodiment of the present invention will be described with reference to the drawings. This embodiment is to detect vibrations generated by termites while eating wood or collecting on wood using a vibration sensor in order to know the invasion of termites. FIGS. 13 and 14 are schematic vertical, sectional views for illustrating two different variations of the fourth embodiment of the present invention.

At the beginning, in FIG. 13, reference numeral 91 designates a detecting device body casing 91, above which a dry cell 92 as a power source is provided. Inside casing 91 there is a signal processing circuit 93 for amplifying and processing signals from a sensor 94 which detects vibratory movement. The casing further accommodates detecting terminal 95 for transmitting vibrations generated by termites to the vibration sensor, a detecting wood sample 96, an elastic member 97 for bringing the wood sample into close contact with detecting terminal 95, a holding tray 98 and a bottom plate 99 of the device.

Next, the termite detecting device constructed as shown in FIG. 13 is typically set on the earth at such an underfloor site as of kitchen or bathroom where termites are likely to develop and proliferate their lives. Since in the underfloor sites, a lot of insects such as ground beetles, sow bugs and any other bugs lead their lives, entrance of such insects, etc., other than termites would cause the sensor to operate or detect erroneously.

For this reason, casing 91 of the detecting device is fixed with a slightest clearance 90 (about 1 mm) spaced from bottom plate 99 of the detecting device. Placing a limitation on the width of clearance in horizontal direction (for example, to about 5 mm) as well as the height can surely prevent such malfunctions.

In the termite detecting device thus constructed, a termite having entered the device through clearance 90 for entrance perceives the presence of the wood sample using its antenna or any other means. If it is a preferable food, the one communicates with other termites and first recognizes it as a 'food'. The termites would 'taste' other parts such as underfloor materials at the time, but since, underfloor materials are usually and mostly made of materials which termites hate, they will finally reach the wood sample placed in the detecting device and eat it.

Since termites destroy the wood sample biting off fibers of wood by their strong jaws, the vibrations generated at the time are transmitted through wood sample 96 to detecting terminal 95 and picked up by vibration sensor 94. At the time, as detecting terminal 95 is made in intimate contact with the surface of wood sample 96 with the help of pressing force by elastic member 97, the vibrations are transmitted relatively smoothly and highly reliably.

However, the vibrations at the time are extremely so delicate that it is impossible to pick it up as it is. The vibrations once converted in the form of electric signals by vibration sensor 94 are amplified in signal processing circuit 93, in which a judgment is made of whether the vibrations are derived from the feeding sound of termites. After the judgment, signal processing circuit 93 issues detection signals as required.

Vibration sensor 94 used in the present embodiment preferably uses a piezoelectric element with a lever directly affixed thereto. Sensors using electromagnetic induction such as a pickup device for phonograph disc may be used other than the above-mentioned element. In the termite detecting system using the termite detecting device of the present invention, it is possible to transmit the signals thus detected by the sensor to a monitoring center by means of a communication terminal such as a modem. This will be described in detail later. Here, in the figure, reference numeral 70 designates a light-reflecting member, which will also be described later.

Next, FIG. 14 shows a variation of the termite detecting device of the embodiment of the present invention.

The same components with those in FIG. 13 are allotted with the corresponding reference numerals and the description is not repeated. In FIG. 14, termites, being attracted by an attractant 96a such as pheromones, etc., prepared in place of wood sample, enter detecting device body 91, and climb up along detecting terminal 95 up to holding tray 98. At this time, since a small gap is provided between bottom plate 99 and the tip of detecting terminal 95, termites must 'wade' across the gap. More clearly, the termite seeks detecting terminal 95 with forelegs while its abdominal segment remaining in contact with bottom plate 99, so as to catch the terminal and hang on it.

As the termites increase in number gradually, the signals become more frequent. Vibration sensor 94 picks up the signals in a similar manner to the above example and the thus picked-up signals are amplified in signal processing circuit 93 and judged therein as to whether or not the signals are derived from an aggregation of termites. After the judgment, signal processing circuit 93 issues detection signals as required.

As another remarkable feature of the present invention, the information on the installation site of the termite detecting device as well as the detected result can be transmitted by way of telephone line to termite-exterminating traders or to various control centers for controlling houses as mentioned before. As shown in a block diagram of FIG. 15, the detected signal by the termite detecting device installed in a house, is transmitted from a terminal net controlling unit 11 to a central apparatus 13 installed in one of various control centers by way of telephone line 12

FIG. 15 shows main components in terminal net controlling unit 11. That is, the unit 11 includes an interface section 14 which receives the contact signal from a magnetic sensor 7 of the termite detecting device, a controlling section 15 which effects transmission control to transmit data on the installation site, etc., a line controlling section 16 for connecting the unit with telephone line 12, and a battery 17 as a power source.

When the destruction by termites is thus detected in the termite detecting device of the present invention basically functioning as has been described heretofore, the termite exterminating trader calls on the user bringing the exterminating apparatus and examines the underfloor space. Upon the examination, the work staff locates the installed site of the detecting device illuminating the space with an portable lamp, etc., and starts the exterminating work targeting the device. However, the device is, in general, hard to find in such a dark place as under the floor.

In such cases, it is very convenient in the practical work if a reflecting member 70 is affixed to the detector body casing as previously shown in FIGS. 13 and 14, in order to allow light from the portable lamp, etc., to be reflected by the reflector. As the reflecting member, it is possible to use publicly known, marketed general products such as an embossed and resin-processed film with aluminum foil, a resin plate in which metallic powder is compounded, and the like. Further, it is more convenient for service if the shape or the way of affixing the reflecting member is made different in order to distinguish the type, year type, setting number, etc., of the device. In addition, by similar way of thinking, it is possible to provide LEDs in order to actively show the position of the device.

In the termite detecting device of the present invention, although a wood piece is used as the detecting sample, this will not limit the sample and it is also possible to use Styrofoam, etc., because the termite is polyphagous insects.

Further, although the foregoing description has been targeted to detect cavitation damaged by termites, the device of the present invention can be applied to detection of deterioration of wood due to putrefactive bacteria and the like or detection of aeration of wood. That is, the device can be applied to detection of time-dependent change of a material which will be made fragile with the passage of time, regardless of whether or not the material is buried in the earth.

As described heretofore, one of main methods of the present invention is to know the destruction of wood caused by termites by pressing and collapsing a detecting sample. Accordingly, when the device is set in an expected invading passage of termites in a house, it is possible to surely find cavitation advancing inside the house by termites in its early stage.

In the device of the present invention, a valid signal is detected using a confined type magnetic sensor, based on the opening of the magnetic path in a magnetic circuit which is composed of, preferably, magnetic substance members having a high-permeability and a low-remanence, or based on the opening of the signal circuit due to cutoff of the signal line. Therefore, it is possible for the device to present enough resistances to varying environment and use in years.

Since, in order to allow the detection terminal to readily sink, the detecting terminal having a domed or spiked tip is abutted against a wood piece as a detecting sample in a direction perpendicular to the annual ring layers of the wood, it is possible to surely detect cavitation that advances inside the wood.

Further, by supplying a proper amount of water to the detecting wood sample for use in the termite detecting device considering the inclination of termites to water, it is possible to achieve a remarkably enhanced performance of attracting termites.

Still more, in the device of the present invention, many clearances are provided everywhere on the periphery of the device body to readily attract termites while earth and sand is put inside an enclosing wall disposed on the case periphery with a detecting wood sample being buried in the earth and sand in the center of enclosed area. By this arrangement, it is possible to surely attract termites in an early stage even if the earth surface is concreted under the floor or no earth surface is exposed.

Moreover, in the present invention, since a guiding pheromone is used as an attractant for termites, it is possible to further enhance the effect on attracting termites.

Further, in the present invention, collecting and aggregation of termites or a state of wood being eaten by termites can be detected as vibrations. This also makes it possible to perform a rapid and assured detection of termites.

Since a reflective member is attached onto the outside surface of the detecting device body casing, it is possible to readily locate the mounted site of the sensor by illuminating with a portable lamp when the damage due to termites is to be examined.

Still, in the present invention, since the detected signal is transmitted from the terminal station to a center, finding and care of houses damaged can be easily conducted over a wide area.

As has been described heretofore, according to the present invention, it is possible to provide a simple termite detecting device that is capable of surely performing around-the-clock monitoring at low cost, and it is possible for the device to surely detect invasion of termites in an early stage and inform a control center of the detected result by means of telephone line before the house under examination is damaged. Accordingly, it is possible to not only simplify termite-extermination but also to make low the cost for protection against termites.

Further, the information on termite-detection is directly transmitted to the termite-extermination trader by way of the control center as well as to or in place of the family of the house, it is possible for the trader to execute the exterminating works strategically. In addition, the reflecting member provided on the device casing allows the exterminating staff for inspection to easily locate the mounted site of the detecting device. This feature is really effective from practical point of view.

What is claimed is:

1. A termite detecting device which is placed in an expected invading passage for detecting damage or destruction caused by termites, comprising:

a detecting wood sample for attracting termites;

a detecting terminal being pressed against said detecting wood sample for transmitting displacement due to the damage or destruction caused by termites; and an elastic member for pressing said detecting terminal and said detecting wood sample against one another;

a magnetic circuit capable of being opened or closed by the displacement of said detecting terminal, said magnetic circuit including a sensor for detecting opening or closing of said magnetic circuit and for generating a detection signal indicating the displacement of said detecting terminal; and water supplying means for supplying water to said detecting wood sample;

whereby detection of termites is carried out based on the detection signal.

2. A termite detecting device according to claim 1, further comprising a controlling means for controlling said water supplying means so as to supply a constant amount of water at regular intervals.

3. A termite detecting device according to claim 1 or 2, wherein supplied water from said water supplying means includes rainwater.

4. A termite detecting device according to claim 1 or 2, wherein supplied water from said water supplying means includes dew condensation water.

5. A termite detecting device according to claim 1 or 2, wherein said water supplying means includes a water reservoir tank.

6. A termite detecting device according to claim 1, wherein said detecting terminal has a tip portion shaped in a dome-like or spike-like form and a barrel portion, the tip having a small sinking resistance.

7. A termite detecting device according to claim 1, wherein said detecting sample is set and buried in earth and sand which fills up inside an enclosed wall provided in the periphery of a casing of said detecting device.

8. A termite detecting device according to claim 1, wherein said detecting sample is a wood piece arranged such that said detecting terminal presses the wood piece in a direction substantially perpendicular to the layers of annual rings of the wood piece.

9. A termite detecting device according to claim 1, wherein said detecting sample is provided with slits.

10. A termite detecting device according to claim 1, further including a casing having clearances for allowing termites to go in and out freely the clearances including a plurality of openings whose size is substantially equal to or in correspondence with the dimension of a termite.

11. A termite detecting device according to claim 1, wherein, in attracting termites, a termite-guiding pheromone is used together with said detecting sample.

12. A termite detecting device according to claim 1, further including a casing, and wherein an outside surface of said casing is affixed with a light-reflecting member serving as an identifying marker.

13. A termite detecting device according to claim 1, further comprising a data transmitting system for transmitting said detection signal from said detecting device to an external, central control center by way of a telephone line and wherein the termite detecting device is integrally controlled by the central control center.

14. An apparatus for detecting termites comprising:

a wood piece as a detecting sample for attracting termites;

a magnetic circuit being composed of, at least, a magnetic substance member as a moving portion and a permanent magnet;

a magnetic sensor disposed in a gap of a magnetic path of said magnetic circuit; and a detecting terminal being attached to said moving portion, and abutting and pressing said wood piece in a direction substantially perpendicular to the layers of annual rings of said wood piece with the help of an elastic member, wherein when said wood piece is eaten and hollowed by termites to become fragile, said detecting terminal sinks into said wood piece thereby shifting said moving portion, the movement of said moving portion opens or shuts down said magnetic circuit, and said magnetic sensor detects the shutdown of said magnetic circuit and issues a valid signal which is in turn terminal-transmitted through telephone line to a certain place so as to be integrally controlled.

15. The apparatus according to claim 14 wherein said wood piece is pressed by said detecting terminal while being supplied with an amount of water.

16. A termite detecting device which is placed in an expected invading passage for detecting damage or destruction caused by termites, comprising:

a detecting sample for attracting termites;

a detecting terminal being pressed against said detecting sample for transmitting displacement due to the damage or destruction caused by termites;

an elastic member for pressing said detecting terminal and said detecting sample against one another;

a moving structure connected to said detecting terminal and capable of displacement by virtue of an elastic pressing force generated by said elastic member and upon damage or destruction to said detecting sample caused by termites; and detection signal generating means for generating a detection signal indicating a displacement of said moving structure, detection of termites being carried out based on the detection signal.

17. A termite detecting device according to claim 16, further comprising:

a fixed member made from a magnetic substance;

a permanent magnet; and a magnetic sensor, wherein said moving structure comprises a magnetic substance while said moving structure, said fixed member and said permanent magnet constitute a magnetic circuit and said magnetic sensor is arranged in a gap of the magnetic circuit.

18. A termite detecting device according to claim 17, wherein the magnetic substance has a high permeability and a low remanence.

19. A termite detecting device according to claim 17 or 1, wherein all the components constituting said magnetic circuit are included within a casing and are hermetically separated from a space in said casing that accommodates said detecting sample.

20. A termite detecting device according to claim 17 or 1, further including a device body containing all the components constituting said magnetic circuit, and a magnetic shield covering said magnetic circuit.

21. A detector for detecting damage or destruction of a wood sample, comprising:

a wood sample;

pheromones for attracting termites to said wood sample;

a detecting terminal in pressing contact with said wood sample;

pressing means for pressing said detecting terminal and said wood sample against one another; and detection signal generating means for detecting displacement of said detecting terminal caused by the damage or destruction of the wood sample and by the pressing of said pressing means, and for generating a detection signal in response to the detected displacement.

22. The detector of claim 21, further comprising a casing for enclosing said wood sample, said detecting terminal, said pressing means, and said detection signal generating means.

23. The detector of claim 22, wherein said casing includes an air-tight space which contains said detection signal generating means.

24. The detector of claim 23, further including:

an inert gas included within the air-tight chamber.

25. A detector for detecting damage or destruction of a wood sample, comprising:

a wood sample;

a detecting terminal in pressing contact with said wood sample;

pressing means for pressing said detecting terminal and said wood sample against one another; and detection signal generating means for detecting displacement of said detecting terminal caused by the damage or destruction of the wood sample and by the pressing of said pressing means, and for generating a detection signal in response to the detected displacement;

a casing for enclosing said wood sample, said detecting terminal, said pressing means, and said detection signal generating means;

a window in said casing; and a displacement mark connected to said detecting terminal, for displacing into visible alignment with said window when said detecting terminal displaces, thereby providing a visible indication that the detecting terminal has displaced.

26. The detector of claim 25, wherein the wood sample is subjectable to damage or destruction caused by termites, the damage or destruction being sufficient to cause the displacement of said detecting terminal.

27. A detector for detecting damage or destruction of a wood sample, comprising:

a wood sample;

a detecting terminal in pressing contact with said wood sample;

pressing means for pressing said detecting terminal and said wood sample against one another; and detection signal generating means for detecting displacement of said detecting terminal caused by the damage or destruction of the wood sample and by the pressing of said pressing means, and for generating a detection signal in response to the detected displacement;

a casing for enclosing said wood sample, said detecting terminal, said pressing means, and said detection signal generating means; and a projection for facilitating the insertion of the detector into the ground.

28. The detector of claim 27, wherein the wood sample is subjectable to damage or destruction caused by termites, the damage or destruction being sufficient to cause the displacement of said detecting terminal.

29. The detector of claim 27, wherein said projection includes a cone-shaped tip for facilitating insertion of the detector into the ground.

30. A device for detecting the time-dependent change of a block of wood, comprising:

a casing;

a block of wood inside said casing, the block of wood including slits;

a detecting terminal inside said casing and pressed against said block of wood;

an elastic member inside said casing producing a pressing force for pressing said detecting terminal and said block of wood against one another, the slits in the wood arranged perpendicular to the pressing force;

a moving structure connected to said detecting terminal and capable of displacement by virtue of the elastic pressing force against said block of wood; and detection signal generating means for detecting displacement of said moving structure and for generating a detection signal indicating the displacement.

31. The device of claim 30, wherein said block of wood is subjectable to damage or destruction caused by termites, the damage or destruction being sufficient to cause the displacement of said moving structure.

32. The device of claim 30, wherein said detection signal generating means further comprises:

a closed magnetic circuit including a permanent magnet, a fixed magnetic substance, a magnetic member disposed on said moving structure and a switch;

wherein displacement of said moving member displaces said magnetic member, thereby opening the magnetic circuit, and wherein said switch detects the opening of the magnetic circuit and generates said detection signal.

33. A device for detecting the time-dependent change of a material, comprising:

a casing;

a material inside said casing;

a detecting terminal inside said casing and pressed against said material;

an elastic member inside said casing producing a pressing force for pressing said detecting terminal and said material against one another;

a moving structure connected to said detecting terminal and capable of displacement by virtue of the elastic pressing force against said material; and detection signal generating means for detecting displacement of said moving structure and for generating a detection signal indicating the displacement; wherein said casing includes:

a first space in which said material and said detecting terminal are disposed;

a second non-enclosed space separated from said first space, said second non-enclosed space defined at a lower edge by a lower case and at a side by an enclosing wall; and earth and sand contained in said second non-enclosed space and in contact with said material.

34. The device of claim 33, further including passing holes disposed in said enclosing wall for permitting passage of termites into and out of said second non-enclosed space, and wherein the time-dependent change of said material is damage or destruction caused by termites.

* * * * *